United States Patent [19]

Wada

[11] Patent Number: 5,063,946
[45] Date of Patent: Nov. 12, 1991

[54] MEASURING METHOD, MEASURING APPARATUS AND INDICATION METHOD OF THE DYNAMICAL CHARACTERISTICS OF MIDDLE EAR

[75] Inventor: Hiroshi Wada, Sendai, Japan

[73] Assignee: Nagashima Medical Instruments Co., Ltd., Japan

[21] Appl. No.: 423,476

[22] Filed: Oct. 18, 1989

[30] Foreign Application Priority Data

Oct. 20, 1988 [JP] Japan .................................. 63-264310

[51] Int. Cl.$^5$ .............................................. A61B 5/00
[52] U.S. Cl. .................................... 128/746; 128/747; 73/585
[58] Field of Search .......................... 128/746, 38, 747; 600/25; 73/589, 585, 648; 381/60, 68, 68.2, 187, 154; 181/196, 130

[56] References Cited

U.S. PATENT DOCUMENTS

| | | | |
|---|---|---|---|
| 3,757,769 | 9/1973 | Arguimbau et al. | 128/746 |
| 4,079,198 | 3/1978 | Bennett | 128/746 |
| 4,251,686 | 2/1981 | Sokolich | 73/585 |
| 4,289,143 | 9/1981 | Cananesio et al. | 128/746 |
| 4,349,083 | 9/1982 | Bennett | 181/130 |
| 4,586,194 | 4/1986 | Kohashi et al. | 73/585 |
| 4,809,708 | 3/1989 | Geisler et al. | 128/746 |
| 4,850,962 | 7/1989 | Schaefer | 128/420.6 |

Primary Examiner—Stephen C. Pellegrino
Assistant Examiner—Robin R. Longo
Attorney, Agent, or Firm—Lowe, Price, LeBlanc & Becker

[57] ABSTRACT

A probe is inserted into an external auditory meatus; the internal pressure of the external auditory meatus is maintained at the predetermined pressure by supplying the air from an air pump connected to one of the sound induction hole; an oscillation signal within the audible range converted into a sound with a predetermined sound pressure is transmitted into the external auditory meatus through another sound induction hole of said probe; and the change in the sound pressure within the external auditory meatus is measured through a microphone. Said probe is to be formed of a hard and relatively thick material and as small as possible in length. Said internal pressure of the external auditory meatus, the frequency of said oscillation signal and the said sound pressure in the external auditory meatus are plotted on a three-dimensional coordinates in order to express three-dimensionally the change in the sound pressure in said external auditory meatus accompanying the change in the impedance of the eardrum surface to the inputted sound where said internal pressure of the external auditory meatus and the frequency of said oscillation signal are given as the parameters.

9 Claims, 12 Drawing Sheets

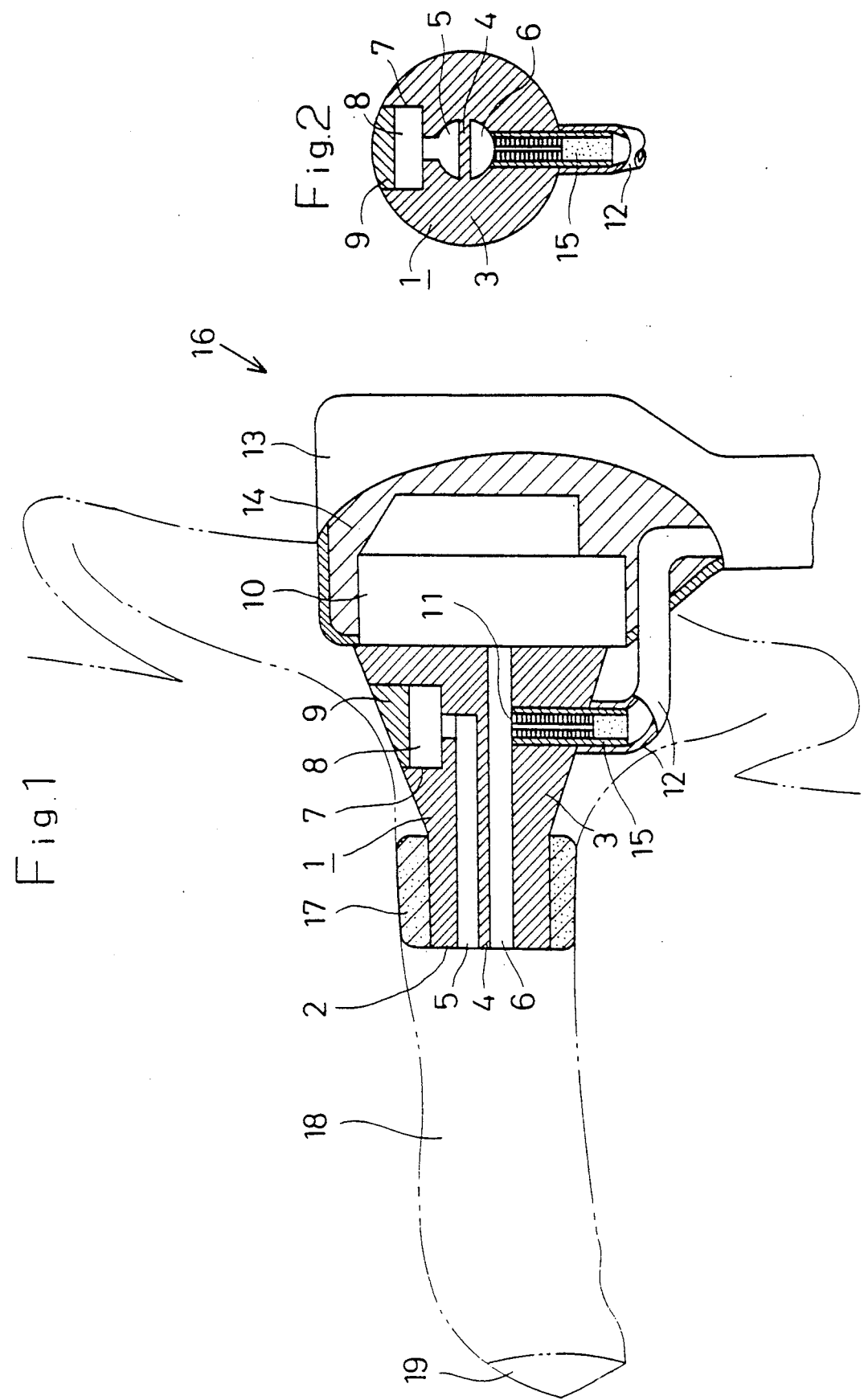

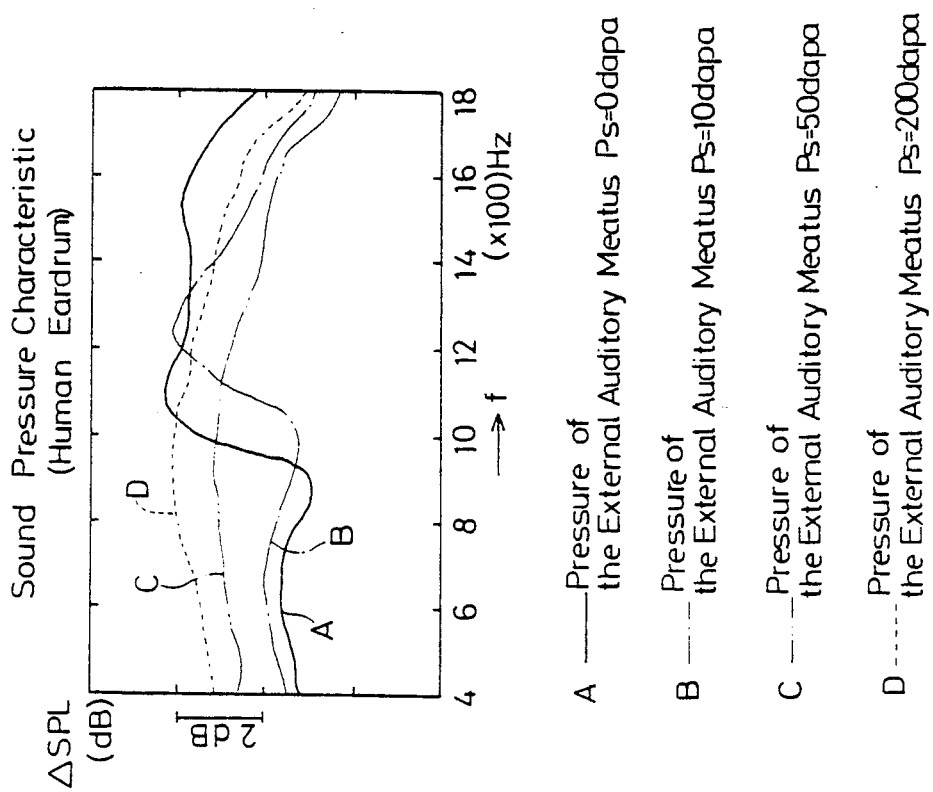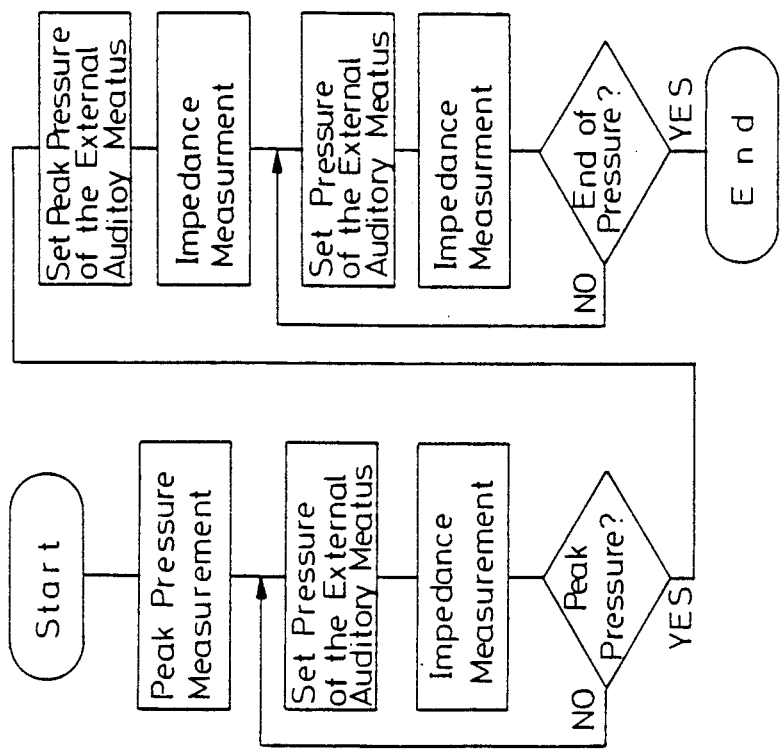

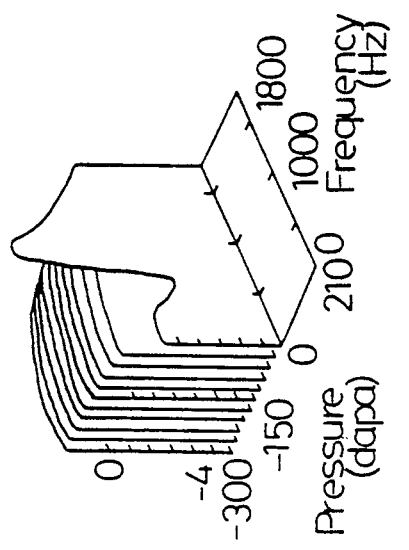
Fig.10(c) View of Pressure 0dapa
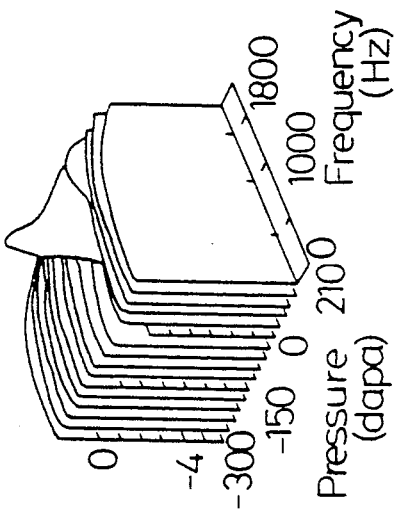
Fig.10(b) View of Pressure 150dapa
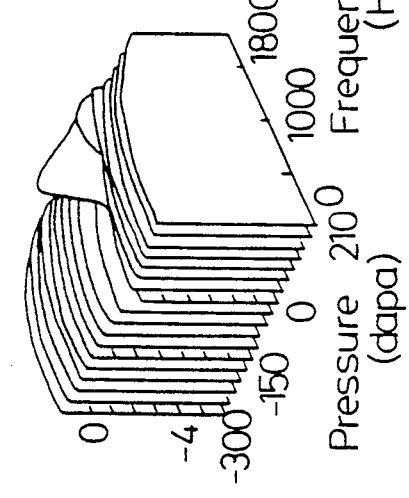
Fig.10(a) Complete View

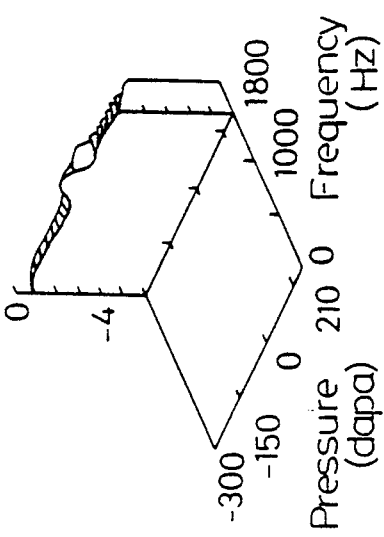
Fig. 10(f) View of Frequency 1500Hz
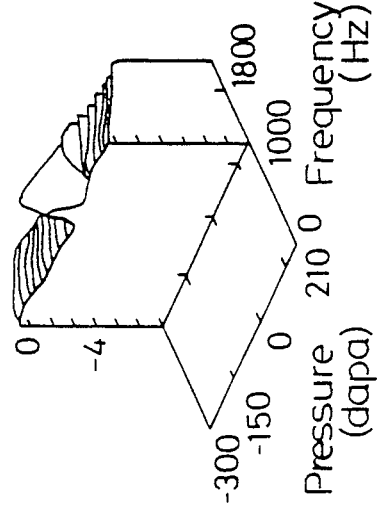
Fig. 10(e) View of Frequency 1000Hz
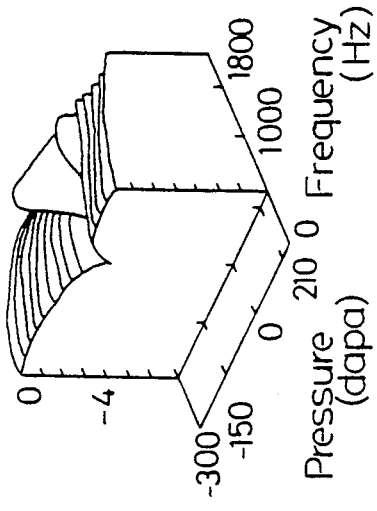
Fig. 10(d) View of Frequency 500Hz Fig. 11(a) Complete View
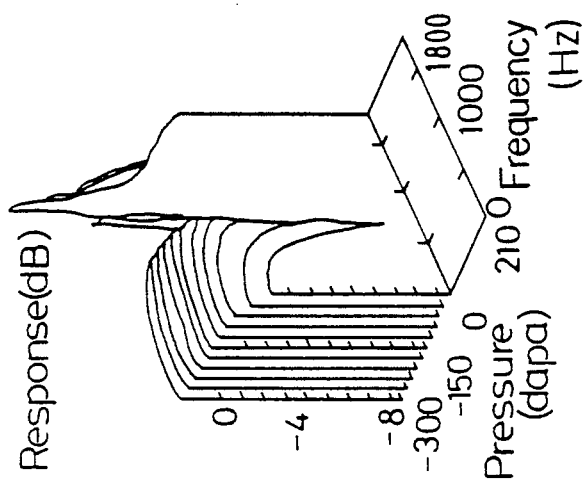
Fig. 11(b) View of Pressure 150dapa
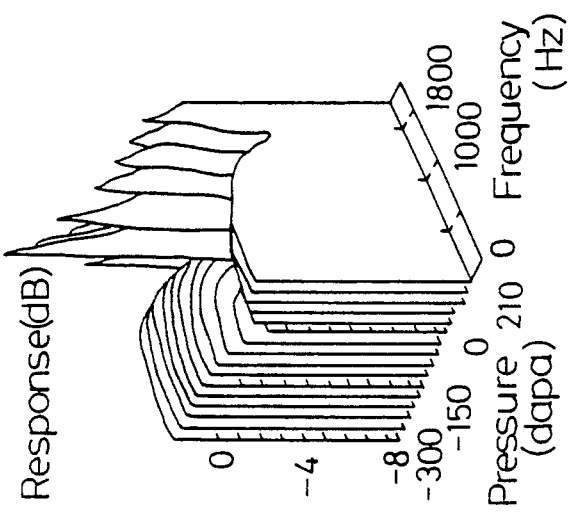
Fig. 11(c) View of Pressure 0dapa
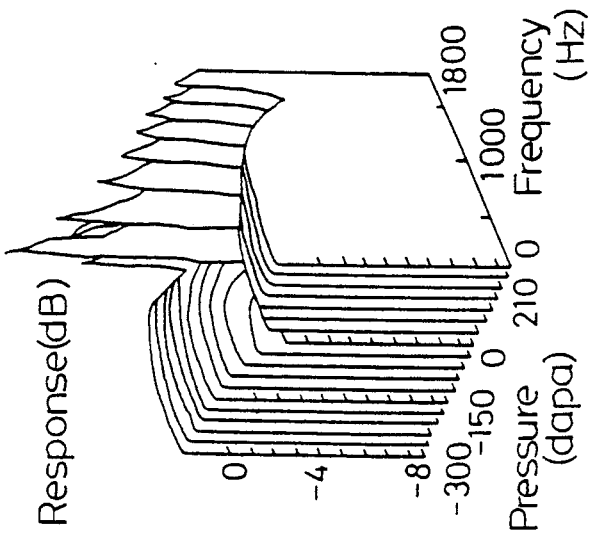

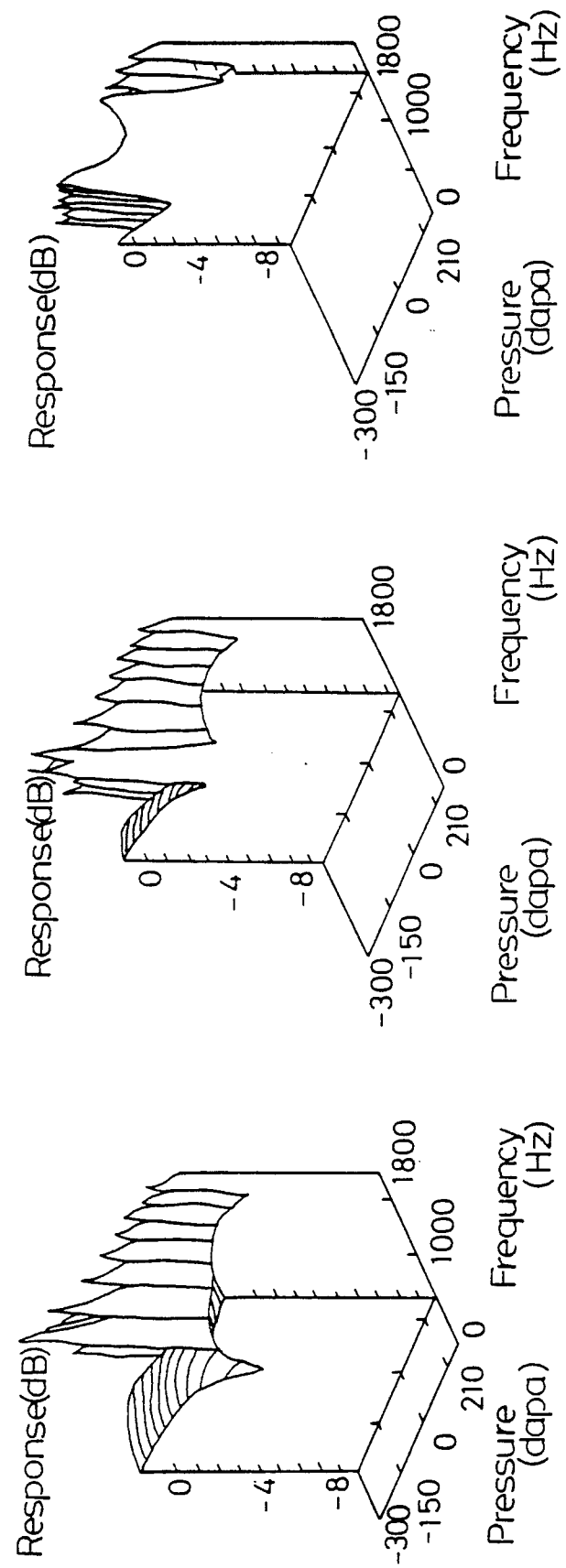

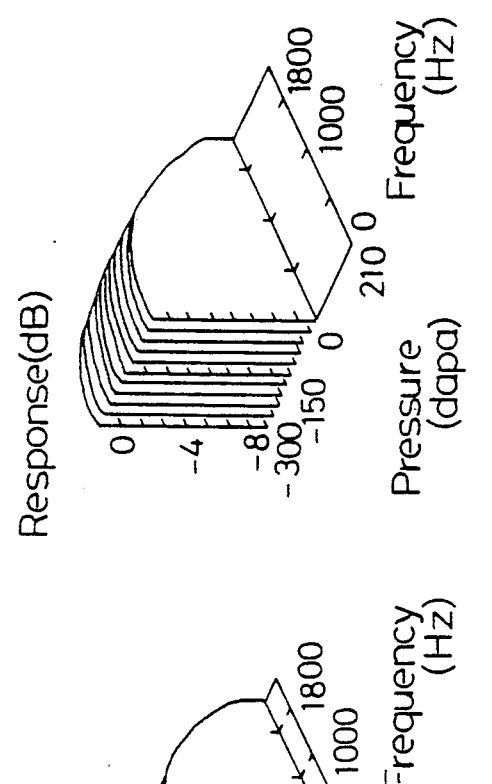
Fig. 12(a) Complete View
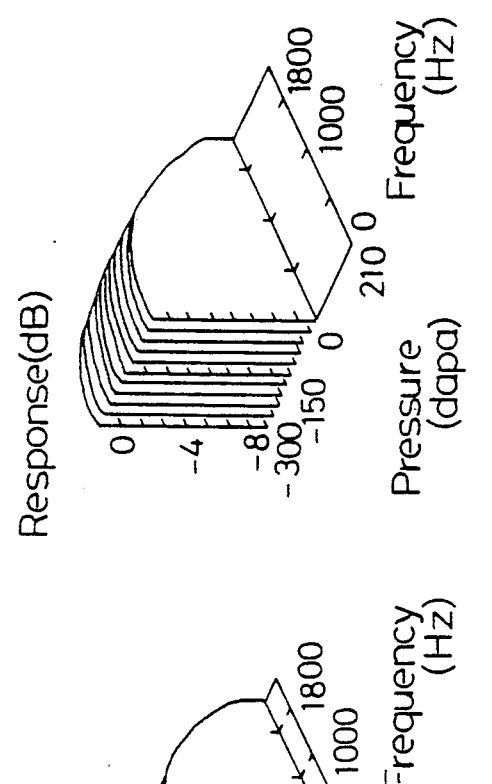
Fig. 12(b) View of Pressure 150 dapa
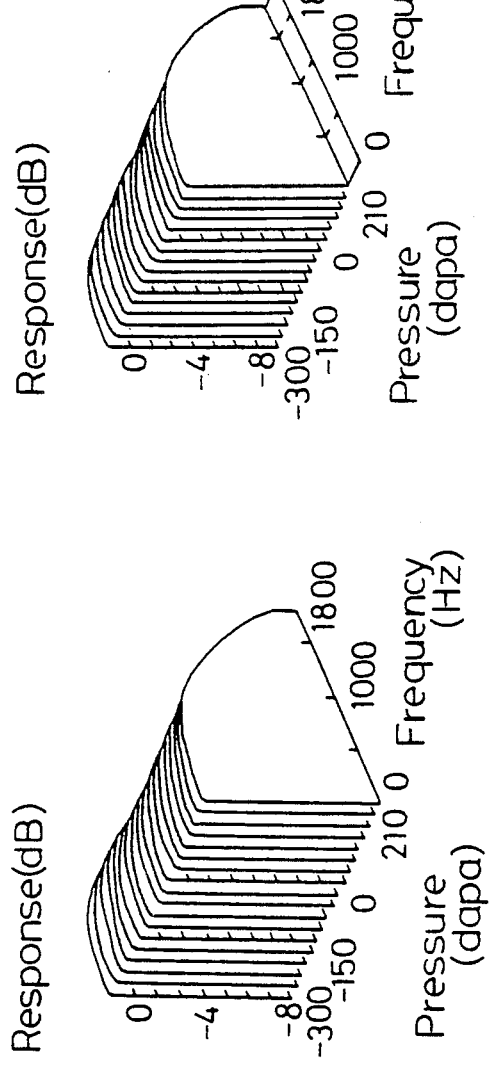
Fig. 12(c) View of Pressure 0 dapa

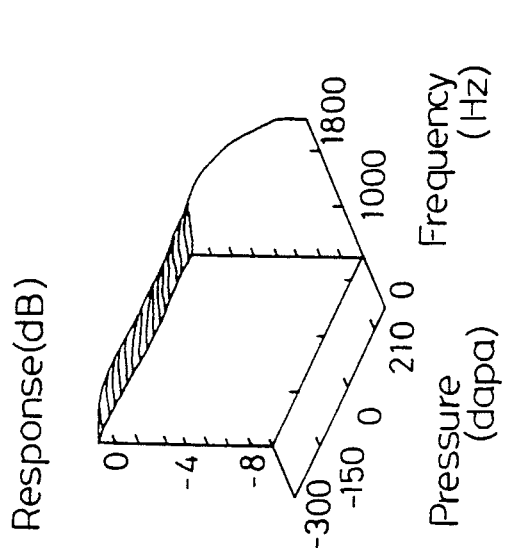
Fig. 12(f) View of Frequency 1500Hz
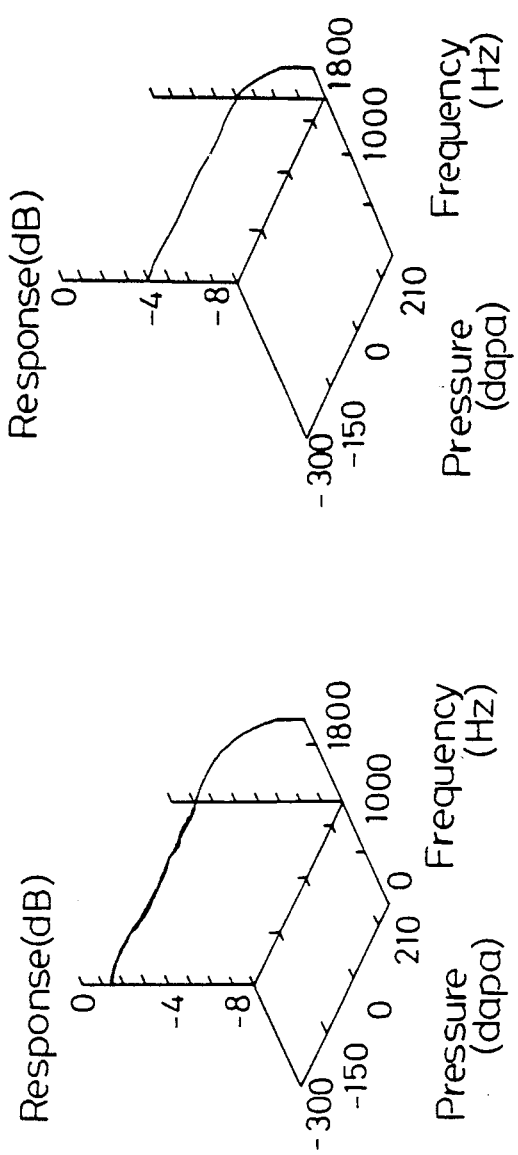
Fig. 12(e) View of Frequency 1000Hz
Fig. 12(d) View of Frequency 500Hz

MEASURING METHOD, MEASURING APPARATUS AND INDICATION METHOD OF THE DYNAMICAL CHARACTERISTICS OF MIDDLE EAR

BACKGROUND OF THE INVENTION

1. Field of the Invention

The present invention relates to a method for measuring the fine change in the dynamical characteristics of the middle ear, the measuring apparatus and the method for indicating the result of the measurement of the dynamical characteristics of the middle ear.

2. Description of the Prior Art

This kind of probe for measuring the dynamical characteristic of the middle ear was disclosed in Japanese Utility Model Publications Nos. 60-168805 and 60-168806. According to these publications, three pieces of stainless steel tubes are passed and fixed to the inside of a member to be inserted into the external auditory meatus; the projected ends of said tubes are respectively connected to the sillicon tubes which communicate with a microphone, an earphone for probe and an earphone for stimulation respectively; and a pressure tube is branched from the tube communicating with the earphone for stimulation to constitute a probe for measuring the dynamical characteristics of the middle ear.

In the case of the above-mentioned conventional probe, however, the insertion member of the probe is connected to the microphone and the earphone with considerably long tubes such as those of 15-22 cm long. As indicated by the solid line, $A_1$ in FIG. 3, the theoretical characteristic of the sound pressure measured by the probe with one end of which is closed is almost flat to the change of the frequency. On the other hand, as indicated by the solid line $A_2$ in FIG. 4, the theoretical characteristic of the phase difference is preferred to increase linearly to the change of the frequency. When the long tubes are used like the case of said conventional probe, however, the acoustic resonance in the tube is relatively small, so that both the sound pressure curve based on the measured value and the phase difference characteristic vary largely with the frequency within the range of the audible frequency as indicated respectively by the broken line $C_1$ in FIG. 3 and by the broken line $C_2$ in FIG. 4, and these are the problems of the conventional probe. Even among the conventional probes, there are some with the tube length reduced to several centimeters, but such tube length is still too large; the tube is made from the soft material such as the vinyl; the wall thickness of the tube is too small; and the body of the probe is made from the soft material such as the plastic, so that the mechanical resonance point is low. As a result, the peak values of the sound pressure characteristic and the phase difference characteristic within the audible frequency range remain at undesirable high levels respectively. Thus, the conventional probes are unable to measure the fine frequency characteristic of the human eardrum.

The present invention provides a middle ear dynamical characteristics measuring apparatus not only capable of measuring the fine frequency characteristic of the human eardrum but also capable of three-dimensionally indicating the result of the measurement by this measuring apparatus so that even those who are lacking in the knowledge of the dynamics will be able to utilize for general diagnosis.

The further objects and characteristics of the present invention will be clarified by the following descriptions.

BRIEF SUMMARY OF THE INVENTION

The present invention relates to a method for measuring the dynamical characteristics of the middle ear using a measuring apparatus comprising a probe body (a sound induction tube) with the sound induction holes, one end of which is closed whereas the other end is closed by an earphone and a microphone, wherein the natural primary frequency $f_1$ of the sound induction tube is larger than the measuring frequency f.

Also, the present invention relates to a middle ear dynamical characteristics measuring apparatus comprising a middle ear dynamical characteristics measuring probe, wherein one of the two sound induction holes is connected to an air pump so that the internal pressure of the external auditory meatus can be increased or decreased; the oscillation signal within audible frequency is converted into the sound of a certain sound pressure level through a microphone; and said sound is transmitted into the external auditory meatus through the other sound induction hole in said probe body to measure the change in the sound pressure in the external auditory meatus and the phase difference between the microphone and the earphone by microphone in the probe body, which is characterized by that said probe body is formed from a hard material and has a relatively large wall thickness, sortest possible length for being able to be fitted into the external auditory meatus, and the sound induction holes are made directly into the probe body.

Further, the present invention relates to a middle ear dynamical characteristics induction method characterized by that the result of the measurement obtained by said measuring method and said measuring apparatus, that is, the internal pressure of the external auditory meatus, the frequency of the oscillation signal and the change in the internal pressure of the external auditory meatus corresponding to the values of the former two factors are plotted on the three-dimensional coordinates so that the change in the internal pressure of the external auditory meatus resulting from the change in the impedance of the eardrum surface to the inputted sound can be indicated three-dimensionally where said internal pressure of the external auditory meatus and said frequency are given as the parameters.

BRIEF DESCRIPTION OF THE DRAWINGS

FIG. 1 is a cross-sectional view of a probe for measuring the dynamical characteristics of the middle ear as one of the embodiment of the present invention.

FIG. 2 is a cross-sectional view along A—A line in FIG. 1.

FIG. 6 is a two-dimensional sound pressure characteristic of a person with normal auditory organ.

FIG. 9 is a flowchart of the measurement by the measuring apparatus illustrated in FIG. 8.

FIG. 10 shows a three-dimensional middle ear dynamical characteristic a person with normal auditory organ.

FIG. 11 is a three-dimensional middle ear dynamical characteristic diagram of a person suffering from the separation of the ossicular chain of the ear.

FIG. 12 is a three-dimensional middle ear dynamical characteristic diagram of a person suffering from the fixation of the ossicular chain of the ear.

DETAILED DESCRIPTION

Figure 4:
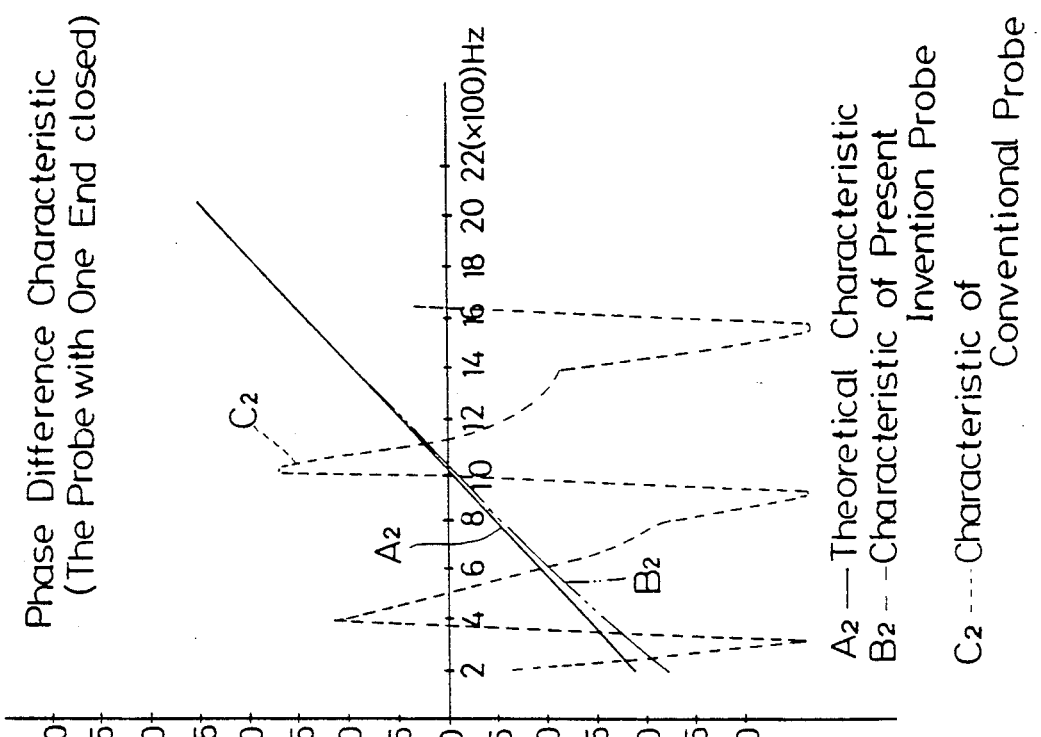
FIG. 4 shows the phase difference characteristic of a probe with one end of which is closed.

The embodiments of the present invention will be explained hereafter in reference to the related drawings.

In FIGS. 1 and 2, the numeral 1 denotes the body of a probe. This probe body 1 is formed from the hard materials such as the metals and the ceramics and comprises a cylindrical insertion member 2 formed at an end of said probe body 1 for insertion into the external auditory meatus and a conical member 3 continuing to said insertion member 2, forming a probe body with overall length of about 19 mm. Said insertion member 2 for the external auditory meatus is about 3-4 mm in outside diameter and contains two semicircular sound induction holes 5 and 6 each with the inside diameter of about 2-3 mm and separated by a center wall 4. One sound induction hole 5 is bent orthogonally at point about 14 mm from its end to communicate with a microphone 8 in a conic member 3. The other sound induction hole 6 passes throughout the base end to communicate with an earphone 10 and branched at the conic member 3 in order to be connected to an air tube 12 containing an acoustic filter 15. An air hole 11 may communicate with another sound induction hole 6.

Said earphone 10 is fully covered with a cover 13 and molded. Said earphone 10 and the microphone 8 are connected to the sound pressure and phase difference measuring circuit shown in FIG. 5, and the air tube 12 is connected to an air pump 23.

Figure 5:
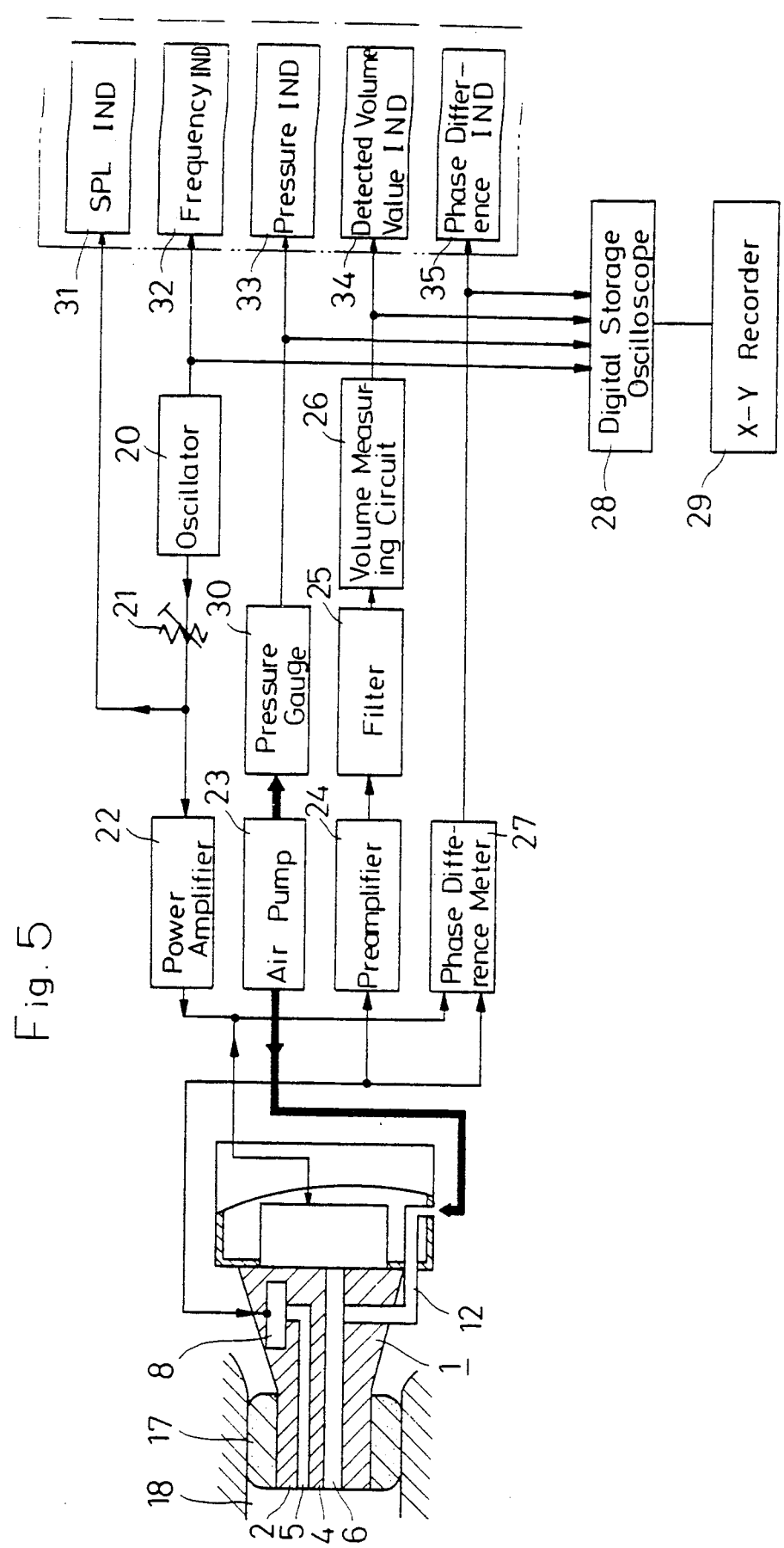
FIG. 5 is a block diagram of a middle ear dynamical characteristic measuring apparatus as an embodiment of the present invention.

The probe 16 having the above-described construction needs to have an earplug 17 mounted around the external circumference of an insertion member 2 for insertion into the external auditory meatus so that the probe can be inserted into the external auditory meatus of the subject for the necessary measurement. The numeral 19 denotes the eardrum. To accomplish the desired measurement with the probe, the signal of sinusoidal waveform obtained by varying the frequency $f_1$ of the signal from an oscillator 20 of the measuring circuit shown in FIG. 5 within the range of 0.1-2.0 KHz by an adjuster 21 is transmitted to the earphone 10 in the sound induction tube 1 through a power amplifier 22 and converted into the sound of a certain sound pressure level through said earphone 10 in order to be introduced into the external auditory meatus 18 by passing one sound induction hole 6 of the sound induction tube 1. The air from the air pump 23 is supplied into the external auditory meatus 18 through the air tube 12, acoustic filter 15 and the sound induction hole 6 in the sound induction tube 1 to increase or decrease the internal pressure of the external auditory meatus 18 within a range of +200 daPa to −200 daPa. The change in the internal pressure of the external auditory meatus 18 is detected by the microphone 8 in the sound induction tube 1, and not only said change in the internal pressure is measured by a volume measuring circuit 26 through a preamplifier 24 and a filter 25 but also the phase difference between the earphone 10 and the microphone 8 is measured by a phase difference meter 27. The information obtained by measurement is once stored in a digital storage oscilloscope 28 and then outputted to an X—Y recorder 29. In FIG. 5, the numeral 30 denotes a pressure gauge; 31, an absolute sound pressure change (SPL) indicator; 32, a frequency indicator; 33, pressure indicator; 34, a detected volume value indicator; and 35, a phase difference indicator.

The reason for that said probe body 1 not only needs to have a from shown in FIG. 1 but also needs to be formed from a hard material can be theoretically proved by the following discussions:

When the probe body 1 to be inserted into the external auditory meatus is considered to be a sort of cantilever, its natural primary frequency $f_1$ can be expressed as $$f_1 = \frac{(1.875)^2}{2\pi} \cdot \frac{1}{l^2} \cdot \sqrt{\frac{E \cdot I}{\rho \cdot A}} \text{ (Hz)}$$

where l, A and represent the length, cross-sectional area and the cross-sectional secondary moment of said probe body 1 respectively, whereas E and $\rho$ represent Young's modulus and the density of the material.

Transforming the above equation into $$f_1 = k \cdot \frac{1}{l^2} \cdot \frac{E}{\rho} \cdot \frac{I}{A}$$

since k is a constant, it is necessary to increase the value of $f_1$ to a value larger than the measured frequency or larger than 2000 Hz, and, in order to satisfy said condition, the value of $$\frac{1}{l^2} \cdot \frac{E}{\rho} \cdot \frac{I}{A}$$

should take a largest possible value. Thus, the following need to be satisfied.

(1) $1/l^2$ should be a largest possible value, or the length should take a smallest possible value.

(2) $E/\rho$ should take a larger value, that is, as to the quality of the material, the density $\rho$ should be relatively small, whereas Young's modulus E should be relatively larger to meet the necessary hardness requirement.

(3) I/A should be relativery large, that is, the thickness of the material should be relativery large.

The probe 16 shown in FIG. 1 is designed to meet all the above requirements.

Figure 3:
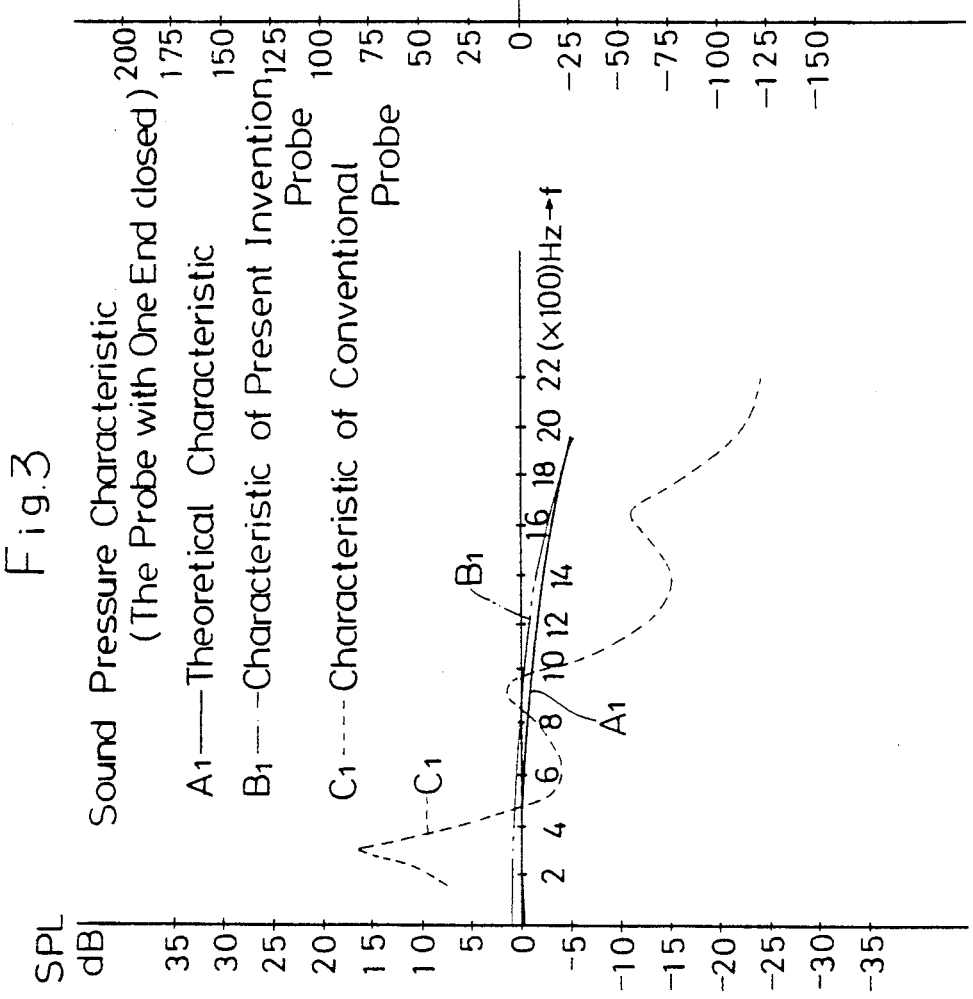
FIG. 3 shows the sound pressure characteristic of a probe with one end of which is closed.

The probe having the above-described construction will have an earplug 17 mounted around the insertion member 2 for insertion into the external auditory meatus as described previously so that the probe can be inserted into the external auditory meatus 18 of the subject for the necessary measurement. With this probe the fine change in the absolute sound pressure and the absolute phase difference of the human eardrum to continuously oscillating frequency can be measured. For instance, the dynamical characteristics (of the middle ear) such as the sound pressure characteristic $B_1$ indicated with the chain-like line in FIG. 3 and the phase difference characteristic $B_2$ indicated with the chain-like line in FIG. 4 agree well with their theoretical values $A_1$ and $A_2$ respectively.

Figure 7:
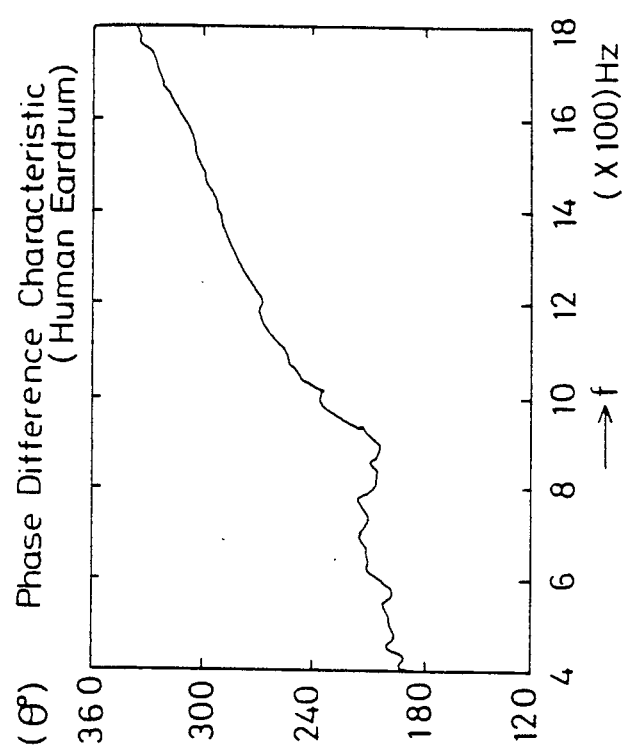
FIG. 7 shows a two-dimensional phase difference characteristic of a person with normal auditory organ.

FIG. 6 shows the sound pressure characteristic of the normal eardrum of a person measured by the probe 16 accoding to the present invention, and FIG. 7, the phase difference characteristic of the same.

The three-dimensional indication of the measured data will be explained hereafter. FIGS. 6 and 7 are the two-dimensional expressions of the measurement result. The two-dimensionally expressed result of the measurement, however, is rather difficult to interprete for those who are lacking in the specialized knowledge of the dynamics, so that the information given in this form is considered to have some difficulty in order to be applied to the general diagnosis.

For example, in the case of the typical measurement result of a person with normal auditory organ shown in FIG. 6 where Ps=0 daPa indicating that the internal pressure Ps of the external auditory meatus almost coincide with the internal pressure of the typanic cavity, a resonance region in which the sound pressure varies appropriately exists around the frequency f=1.0 KHz. This resonance region moves towards the region of higher frequency as the value of Ps increases, and the variation ratio of the sound pressure within the resonance region becomes smaller. The drag (the spring stiffness or impedance) of the eardrum surface to the inputted sound can be considered to be the sum of the drag of the eardrum itself, the drag of the auditory ossicular chain exerted on the eardrum and the drag of the middle ear pneumatic space exerted on the eardrum. Then, it can be considered that sum of these drags and the inertias of the eardrum, auditory ossicular chain and middle ear pneumatic space are balanced to form a resonance region around f=0.1 KHz. Also, the appropriate variation, not too larger nor too small, occurring within the resonance region can be considered to occur due to the appropriate attenuation (of the inertias) of the eardrum, auditory ossicular chain and middle ear pneumatic space. The increase in the value of Ps mainly causes the increase of the drag and attenuation of the auditory ossicular chain (the dependency of the auditory ossicular chain on the pressure). As a result, the resonance region moves towards the range of higher frequency, and this seems to cause the decrease in the sound pressure variation ratio within the resonance region.

In the case of the measurement result shown in FIG. 6, Ps is taken as a parameter, so that the number of the curves representing the measurement result which can be indicated is naturally limited, and thus the changes in the dynamical characteristics of the middle ear according to various values of Ps cannot be indicated. Besides, it is difficult to compare the result of the measurement with the widely spread tympanogram, since the result of the measurement represents the change of the sound pressure to the frequency.

Figure 8:
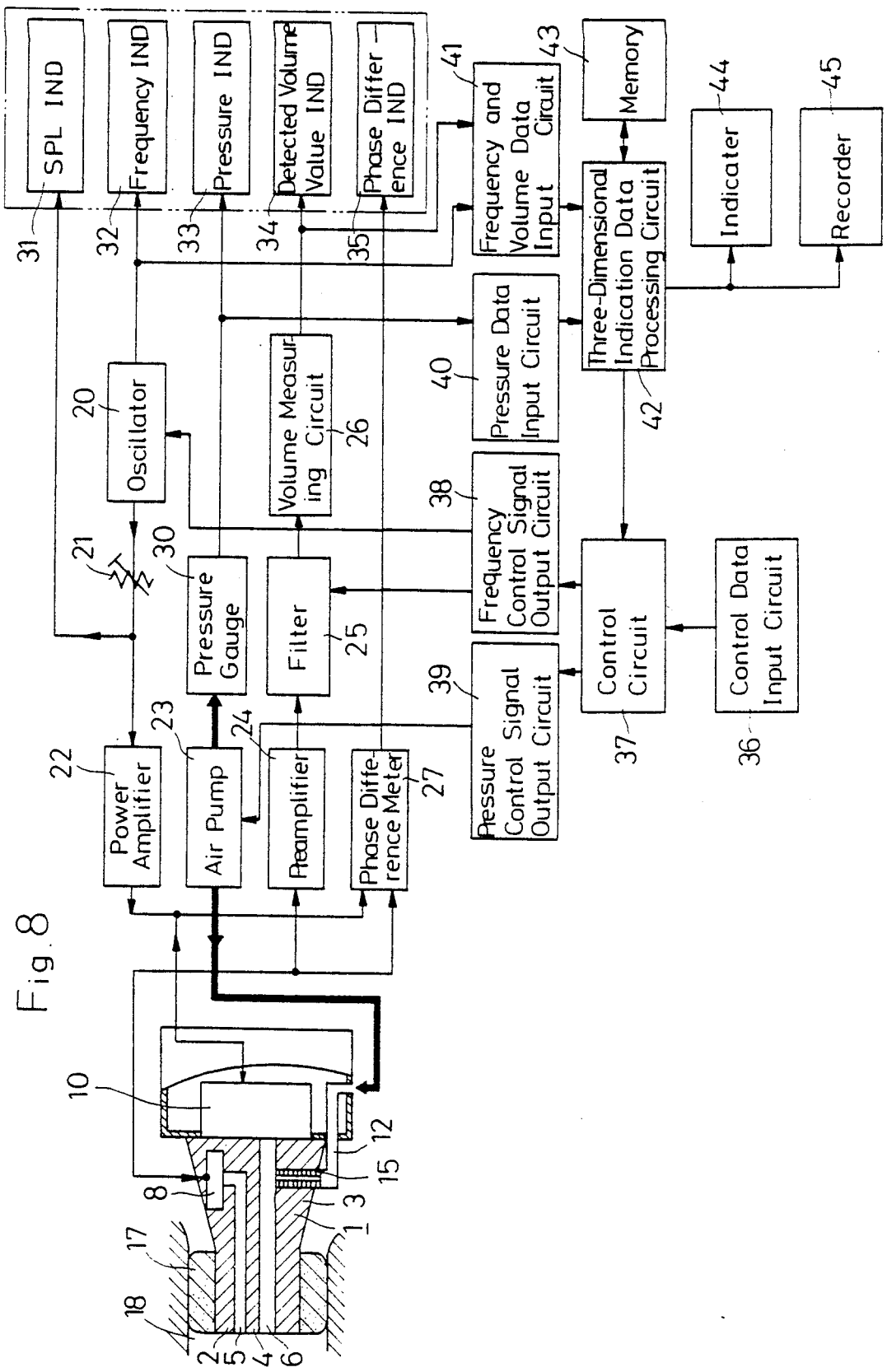
FIG. 8 is a block diagram of the middle ear dynamical characteristic measuring apparatus as the second embodiment of the present invention.

Thus, the measuring apparatus is composed as shown in FIG. 8 replacing the digital storage oscilloscope 28 and the X—Y recorder 29. More particularly, a pressure gauge 30 is connected to a pressure data input circuit 40; a oscillator 20 and the volume detection circuit 26 are connected to a frequency and volume data input circuit 41; and these data input circuits 40 and 41 are connected to a three-dimensional indication data processing circuit 42. Said three-dimensional indication data processing circuit 42 is connected to a memory 43, indicator 44, recorder 45 and the control circuit 37. Said control circuit 37 is connected to said air pump 23 through a pressure control signal output circuit 39, to said filter 25 and the oscillator 20 through a frequency control signal output circuit 38 and to a control data input circuit 36.

The measurement process by the measuring apparatus composed incorporating the above-described components will be explained hereafter according to the flowchart shown in FIG. 9.

The peak pressure of the eardrum as an object of the measurement is measured first. For this measurement, the frequency f of the oscillator 20 is set to a certain value by the command from the control data input circuit 36 which will be transmitted through the control circuit 37 and the frequency control signal output circuit 38. In this case, normaly the frequency is set to 220 Hz. The signal of 220 Hz (f=220 Hz) having sinusoidal waveform is transmitted to the earphone 10 in the probe body 1 through a power amplifier 22 and converted into the sound of a certain sound pressure in order to be introduced into the external auditory meatus 18 passing through one sound induction hole 6 of the probe body 1. Similarly, the air pump 23 is controlled by the command from the control data input circuit 36 which is transmitted through the control circuit 37 and the pressure control signal output circuit 39. The air from said air pump 23 is supplied into the external auditory meatus 18 by way of the air tube 12, acoustic filter 15 and the sound induction hole 6 of the probe body 1 to increase or decrease the internal pressure of the external auditory meatus 18 within a range of +210 daPa to −300 daPa. The change in the sound pressure (the impedance) within the external auditory meatus 18 is detected by the microphone 8 in the probe body 1, and the detected sound pressure is measured by the volume detection circuit 26 through the preamplifier 24 and the filter 25. Simultaneously, the phase difference between the earphone 10 and the microphone 8 is measured by the phase difference meter 27. Of these data, the pressure data is stored in the memory 43 through the pressure data input circuit, whereas the impedance is stored in the same memory through the volume data input circuit 41 and the three-dimensional indication data processing circuit 42, and said data are two-dimensionally indicated on the indicator 44 and recorder 45. The peak value of the internal pressure Ps of external auditory meatus is measured from said two-dimensionally indicated data. In this case, the value of Ps is assumed, for example, to be 0.

Then, the pressure is increased, for example, by every 30 daPa by the command from the control data circuit which is transmitted through the pressure control signal output circuit 39, and the frequency of the oscillator 20 is made variable within a range of 0–1800 Hz by the command from the control data input circuit 36 which is transmitted through the control circuit 37 and the frequency control signal output circuit 38, whereby the characteristic X shown in FIG. 10(a) can be obtained, and these data are also stored in the memory 43.

Similarly, the data is obtained for every 30 daPa until said peak value, Ps=0, is reached, and the data are stored in the memory 43. Where the data is taken for every 30 daPa, said peak value, Ps=0, is not always reached, and so it is necessary to set the value to Ps=0 to measure the impedance similarly. Furthermore, the impedance is measured sequentially for every 30 daPa until the value of Ps reaches −300 daPa even on the minus side.

The data obtained in this manner are all stored in the memory 43. From said stored data, the frequency f, the internal pressure Ps of the external auditory meatus and the impedance (dB) are plotted on the X, Y and Z axes respectively by the three-dimensional indication data processing circuit 42 as shown in FIGS. 10, 11 and 12 respectively for the three-dimensional indication of these data, and the processed data are not only indicated on the indicator 44 but also recorded by the recorder 45.

Of these three dimensional characteristic diagrams, FIG. 10 represents the case of a person with normal auditory organ. According to this diagram, a resonance region in which the sound pressure varies largely is recognized around f=1.0 KHz in the vicinity of Ps=0 daPa; the resonance region moves gradually towards the range of higher frequency as the difference between Ps and the internal pressure of the tympanic cavity increases, and the variation ratio of the sound pressure decreases; and it is recognized that the resonance region disappears completely when Ps=200 and −300 daPa. FIG. 11 shows the result of the measurement concerning a patient suffering from the separation of auditory ossicular chain. In this case, it can be recognized that the sound pressure variation in the vicinity of Ps=0 daPa is much larger than that of the person with normal auditory organ; the frequency of the resonance region increases as the value of Ps increase or decrease, and the sound pressure variation ratio decreases, but the resonance region can still be recognized definitely even where Ps=200 and −300 daPa. FIG. 12 shows the result of the measurement concerning the patient suffering from the fixation of the auditory ossicular chain. In this case, we can notice that the resonance region is not recognized at any value of Ps, and the movement of the eardrum surface is restrained.

Furthermore, the characteristic diagram representing the cases where Ps or f is fixed to a certain value can readily be obtained as shown in FIGS. 10(b) through (f), FIGS. 11(b) through (f) and FIGS. 12(b) through (f).

What is claimed is:

1. A middle ear dynamical characteristics measuring method using a sound indication tube with an open ear insertion end and an opposite end closed with an earphone and a microphone, comprising the steps of:
   selecting a geometry of said sound induction such that a natural primary frequency $f_1$ of said sound induction tube is larger than a measurement frequency f within a range of 0.1 to 2.0 KHz;
   generating a test audio signal having said measurement frequency;
   supplying an audible signal into the ear in response to said test audio signal using said earphone;
   controlling a static air pressure within the ear;
   detecting an audible signal in the ear and, in response, supplying a detected audio signal;
   measuring sound pressure within the ear in response to said detected audio signal and, in response, supplying sound pressure data; and
   measuring a phase relationship between said test audio signal and said detected audio signal.

2. A middle ear dynamical characteristics mesuring method defined in claim 1, where the natural frequency $f_1$ of the sound induction tube determined as $$f_1 = k \cdot \frac{1}{l^2} \cdot \frac{E \cdot I}{\rho \cdot A}$$

where k is a constant; , A and I are the length, cross-sectional area and the cross-sectional secondary moment of the sound induction tube respectively; and E and $\rho$ are the Young's modulus and the density of the material respectively.

3. A middle ear dynamical characteristics measuring method in accordance with claim 1, further comprising the steps of:
   storing said sound pressure data in a memory;
   detecting a peak value of sound pressure within the ear;
   progressively changing said static air pressure within the ear over a predetermined range; and
   progressively changing said frequency of said test audio signal generated by said generating step.

4. A middle ear dynamical characteristics measuring method in accordance with claim 3, further comprising the step of graphically plotting said sound pressure data versus said static air pressure and said test audio frequency.

5. A middle ear dynamical characteristics measuring probe, comprising:
   a probe body insertable in an external auditory meatus;
   two induction holes in said probe body;
   means for connecting one of said two induction holes to an air pump;
   means for controlling said air pump to increase or decrease an internal air pressure of the external auditory meatus;
   means for supplying a test signal having an audible frequency;
   an earphone receiving said test signal and converting said test signal into a corresponding audible sound having a predetermined sound pressure;
   means for transmitting said audible sound into said auditory meatus through one of said induction holes of said probe body;
   a microphone for detecting a sound imparted to said external-auditory meatus and, in response, supplying a detected audio signal;
   means responsive to said detected audio signal for measuring a change of a detected sound induced pressure in said external auditory meatus; and
   means responsive to said test signal and to said detected audio signal for detecting a phase difference between a measured sound imparted to said external auditory meatus and said audible sound transmitted thereto;
   wherein the induction hole communicating with the earphone and the other induction hole communicating with the microphone each have semicircular cross sections disposed opposing to each other by being separated by a central partition wall.

6. A middle ear dynamical characteristics measuring probe according to claim 5, wherein the probe body is formed from a material selected from the group consisting of stainless steel, iron and ceramics.

7. A middle ear dynamical characteristics measuring probe defined in claim 5, wherein the length of each sound induction hole of the probe body is between 10 and 30 mm.

8. A three-dimensional middle ear dynamical characteristics indication method comprising the steps of:
   varying an internal static pressure of an external auditory meatus;
   supplying an audible stimulating signal into said external auditory meatus;
   sensing, in said external auditory meatus, an audible resultant signal produced in response to said stimulating audible signal;

detecting a phase difference between said stimulating audible signal and said resultant signal; and plotting a frequency of said audible stimulating signal, an internal static pressure of the external auditory meatus and a change in an internal dynamic pressure of the external auditory meatus on three-dimensional coordinates so that the change in the internal dynamic pressure of the external auditory meatus resulting from a change in the impedance of an eardrum surface to the audible stimulating signal are indicated in three-dimensions where said internal static pressure of the external auditory meatus and the frequency of said audible stimulating signal are given as parameters.

9. A middle ear dynamical characteristics measuring apparatus, comprising:

a probe body;

two sound induction holes in the probe body, one of said induction holes having means for connecting said one hole to an air pump operable to control an internal pressure of an external auditory meatus;

generator means for supplying an audio signal;

transducer means receiving said audio signal and, in response, supplying an audible sound signal with a predetermined sound pressure and transmitted into the external auditory meatus through one of the sound induction holes in said probe body;

a microphone in said probe body for sensing an internal pressure of the external meatus;

means responsive to an output from said microphone for detecting and measuring a change in said internal pressure of said external auditory meatus and, in response, providing corresponding pressure data; and a control circuit for controlling (i) a pressure of said air pump, (ii) a frequency of said audio signal, and (iii) a three-dimensional data processing circuit for displaying a three-dimensional representation of pressure data.

* * * * *